United States Patent
Mansfield et al.

(10) Patent No.: US 7,754,741 B2
(45) Date of Patent: Jul. 13, 2010

(54) PYRIDINE DERIVATIVES AS FUNGICIDAL COMPOUNDS

(75) Inventors: Darren James Mansfield, Lyons (FR); Heiko Rieck, Sainte Foy-les-Lyons (FR); Jörg Greul, Leicglingen (DE); Pierre-Yves Coqueron, Lyons (FR); Philippe Desbordes, Lyons (FR); Pierre Genix, Lyons (FR); Marie-Claire Grosjean-Cournoyer, Curis au Mont d'Or (FR); Joseph Perez, Lyons (FR); Alain Villier, Saint Didier Au Mont d'Or (FR)

(73) Assignee: Bayer Cropscience S.A. (FR)

( * ) Notice: Subject to any disclaimer, the term of this patent is extended or adjusted under 35 U.S.C. 154(b) by 16 days.

(21) Appl. No.: 10/545,364

(22) PCT Filed: Feb. 12, 2004

(86) PCT No.: PCT/EP2004/002381

§ 371 (c)(1),
(2), (4) Date: Sep. 20, 2005

(87) PCT Pub. No.: WO2004/074280

PCT Pub. Date: Sep. 2, 2004

(65) Prior Publication Data

US 2006/0052366 A1    Mar. 9, 2006

(30) Foreign Application Priority Data

Feb. 19, 2003    (EP) .................................. 03356029

(51) Int. Cl.
*A61K 31/44* (2006.01)
*C07D 213/04* (2006.01)
*C07D 213/62* (2006.01)
(52) U.S. Cl. ........................ 514/340; 546/255; 546/261
(58) Field of Classification Search ................ 540/484, 540/553; 544/1; 546/1, 255, 261; 548/100; 514/340
See application file for complete search history.

(56) References Cited

FOREIGN PATENT DOCUMENTS

| GB | 1386965 | 3/1975 |
|----|---------|--------|
| WO | WO 00/21934 | 4/2000 |
| WO | WO 01/11965 | 2/2001 |
| WO | WO-0111965 | * 2/2001 |

OTHER PUBLICATIONS

Wrobel et al, Spiro derivatives of tetrahydrothiophene. Phase transfer catalyzed alkylation of the synthesis of spiro quinolizidine derivative, Bulletin of the Polish Academy of Science, Chemistry, 1987, 35 No. 1-2, 21-9.*

* cited by examiner

*Primary Examiner*—Alton N Pryor

(57) ABSTRACT

Compound of general formula (I): Process for preparing this compound. Novel intermediate of general formula (E): for the preparation of compound of general formula (I) Fungicidal composition comprising a compound of general formula (I). Method for treating plants by applying a compound of general formula (I) or a composition comprising it.

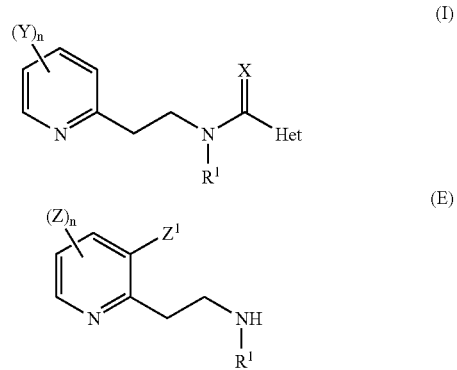

23 Claims, No Drawings

PYRIDINE DERIVATIVES AS FUNGICIDAL COMPOUNDS

CROSS-REFERENCE TO RELATED APPLICATIONS

The present application is a 35 U.S.C. §371 national phase conversion of International Application No. PCT/EP2004/002381 filed Feb. 12, 2004, which claims priority of European Application No. 03356029.3 filed Feb. 19, 2003.

The present invention relates to novel N-[2-(2-pyridinyl)ethyl]carboxamides derivatives, their process of preparation, their use as fungicides, particularly in the form of fungicidal compositions, and methods for the control of phytopathogenic fungi of plants using these compounds or their compositions.

The international patent application WO 01/11965 discloses a broad family of fungicidal compounds which generically covers the compounds according to the present invention. Nevertheless, the compounds according to the present invention are not specifically disclosed in this document and their activity as fungicides has not been tested.

It is always of high-interest in agriculture to use pesticidal compounds more active than the compounds already known by the man ordinary skilled in the art in order to decrease the quantity of active ingredient used by the farmer as to maintain an efficacy at least equivalent to compounds already known.

We have now found a new family of compounds selected in a broad family of compounds which possess the above mentioned characteristics.

Accordingly, the present invention relates to N-[2-(2-pyridinyl)ethyl]carboxamide derivative of general formula (I):

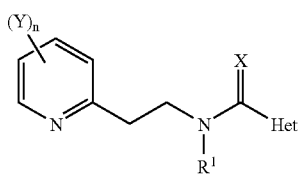

(I)

in which:

X may be an oxygen atom or a sulphur atom;

Y may be the same or different and may be a halogen atom, a nitro group, a cyano group, a hydroxy, a carboxzyl group, a $C_1$-$C_8$-alkyl, a $C_1$-$C_6$-halogenoalkyl having 1 to 5 halogen atoms, a $C_1$-$C_8$-alkylamino, a di-$C_1$-$C_8$-alkylamino, a $C_1$-$C_8$-alkoxy, a $C_1$-$C_6$-halogenoalkoxy having 1 to 5 halogen atoms, a $C_1$-$C_8$-alkylthio, a $C_1$-$C_6$-halogenoalkylthio having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkinyloxy, a $C_3$-$C_8$-halogenoalkinyloxy having 1 to 5 halogen atoms, a $C_3$-$C_8$-cycloalkyl, a $C_1$-$C_8$-alkoxycarbonyl, a $C_1$-$C_8$-alkylsulphinyl, a $C_1$-$C_8$-alkylsulphonyl, a $C_1$-$C_8$-halogenoalkylsulphinyl having 1 to 5 halogen atoms, a $C_1$-$C_8$-halogenoalkylsulphonyl having 1 to 5 halogen atoms or a $C_1$-$C_6$-alkoximino-$C_1$-$C_6$-alkyl;

$R^1$ may be a hydrogen atom, a cyano group, a nitro group, a formyl group, a $C_1$-$C_6$-alkyl, a $C_1$-$C_6$-alkylcarbamoyl, a $C_2$-$C_6$-alkenyl, a $C_2$-$C_6$-alkynyl, a $C_1$-$C_6$-halogenoalkyl having 1 to 7 halogen atoms, a $C_1$-$C_6$-alkoxy-$C_1$-$C_6$-alkyl, a $C_1$-$C_6$-cyanalkyl, a $C_1$-$C_6$-aminoalkyl, a $C_3$-$C_6$-cycloalkyl, a $C_1$-$C_6$-alkylcarbonyl, a $C_1$-$C_6$-halogenalkylcarbonyl having 1 to 5 halogen atoms, a $C_1$-$C_6$-alkoxy-$C_1$-$C_6$-alkylcarbonyl, a $C_1$-$C_6$-alkylsulfanyl or a $C_1$-$C_6$-halogenalkylsulfanyl having 1 to 5 halogen atoms;

n maybe 1, 2, 3 or 4; and

Het represents an optionally substituted 5-, 6- or 7-membered non-fused heterocycle with one, two or three heteroatoms which may be the same or different; Het being linked by a carbon atom.

In the context of the present invention:
halogen means fluorine, bromine, chlorine or iodine;
heteroatom means N, O or S.

According to the present invention, X represents an oxygen atom or a sulphur atom. Preferably, X represents an oxygen atom.

According to the present invention, the 2-pyridyl may be substituted in every position by $(Y)_n$, in which Y and n are as defined above. Preferably, the present invention relates to N-[2-(2-pyridinyl)ethyl]carboxamide derivative of general formula (I) in which the different characteristics may be chosen alone or in combination as being:

as regards n, n is 1 or 2. More preferably n is 2.

as regards Y, at least one of the Y substituent is a halogen atom, a $C_1$-$C_8$-alkyl, a $C_1$-$C_6$-halogenoalkyl having 1 to 5 halogen atoms or a $C_1$-$C_6$-alkoxy-$C_1$-$C_6$-alkylcarbonyl. More preferably, at least one of the Y substituent is a $C_1$-$C_6$-halogenoalkyl having 1 to 5 halogen atoms. Even more preferably, at least one of the Y substituent is —$CF_3$.

as regards the positions in which the 2-pyridyl is substituted, the 2-pyridyl is substituted in 3- and/or in 5-position.

Even more preferably, the substituent in 5-position is —$CF_3$.

According to the present invention, "Het" of the compound of general formula (I) may be a five membered ring non-fused heterocycle. Specific examples of compounds of the present invention where Het is a five membered heterocycle include:

Het represents a heterocycle of the general formula (II)

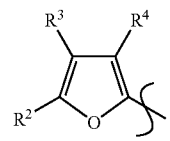

(II)

in which:

$R^2$ and $R^3$ may be the same or different and may be a hydrogen atom, a halogen atom, an amino group, a nitro group, a $C_1$-$C_4$-alkyl or a $C_1$-$C_4$-halogenoalkyl having 1 to 5 halogen atoms; and $R^4$ may be a hydrogen atom, a halogen atom, a nitro group, a $C_1$-$C_4$-alkyl or a $C_1$-$C_4$-halogenoalkyl having 1 to 5 halogen atoms.

Het represents a heterocycle of the general formula (III)

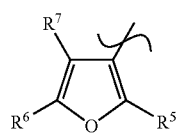

(III)

in which:
- R⁵ may be a hydrogen atom, a halogen atom, a $C_1$-$C_4$-alkyl or a $C_1$-$C_4$-halogenoalkyl having 1 to 5 halogen atoms; and
- R⁶ and R7⁶ may be the same or different and may be a hydrogen atom, a halogen atom, an amino group, a $C_1$-$C_4$-alkyl or a $C_1$-$C_4$-halogenoalkyl having 1 to 5 halogen atoms.

Het represents a heterocycle of the general formula (IV)

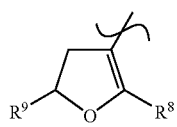

(IV)

in which:
- R⁸ may be a halogen atom, a $C_1$-$C_4$-alkyl or a $C_1$-$C_4$-halogenoalkyl having 1 to 5 halogen atoms; and
- R⁹ may be a hydrogen atom, a $C_1$-$C_4$-alkyl or a $C_1$-$C_4$-halogenoalkyl having 1 to 5 halogen atoms.

Het represents a heterocycle of the general formula (V)

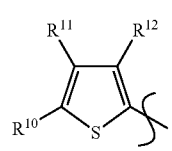

(V)

in which:
- R¹⁰ and R¹¹ may be the same or different and may be a hydrogen atom, a halogen atom, a $C_1$-$C_4$-alkyl, a $C_1$-$C_4$-halogenoalkyl having 1 to 5 halogen atoms, a $C_1$-$C_4$-alkylthio, a $C_1$-$C_4$-alkylsulphonyl, a phenyl optionally substituted by a halogen atom or a $C_1$-$C_4$-alkyl or a pyridyl optionally substituted by a halogen atom or a $C_1$-$C_4$-alkyl; and
- R¹² may be a hydrogen atom, a halogen atom, a cyano group, a $C_1$-$C_4$-alkyl, a $C_1$-$C_4$-halogenoalkyl having 1 to 5 halogen atoms or a $C_1$-$C_4$-halogenoalkoxy having 1 to 5 halogen atoms.

Het represents a heterocycle of the general formula (VI)

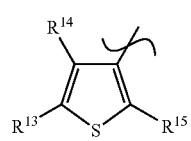

(VI)

in which:
- R¹³ and R¹⁴ may be the same or different and may be a hydrogen atom, a halogen atom, a $C_1$-$C_4$-alkyl, a $C_1$-$C_4$-alkyloxy or a $C_1$-$C_4$-halogenoalkyl having 1 to 5 halogen atoms; and
- R¹⁵ may be a hydrogen atom, a halogen atom, a $C_1$-$C_4$-alkyl or a $C_1$-$C_4$-halogenoalkyl having 1 to 5 halogen atoms.

Het represents a heterocycle of the general formula (VII)

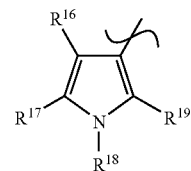

(VII)

in which:
- R¹⁶ may be a hydrogen atom, a halogen atom, a cyano group, a $C_1$-$C_4$-alkyl or a $C_1$-$C_4$-halogenoalkyl having 1 to 5 halogen atoms;
- R¹⁷ and R¹⁹ may be the same or different and may be a hydrogen atom, a halogen atom, a $C_1$-$C_4$-alkyl or a $C_1$-$C_4$-halogenoalkyl having 1 to 5 halogen atoms; and
- R¹⁸ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl.

Het represents a heterocycle of the general formula (VIII)

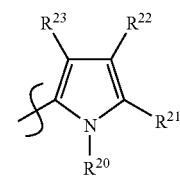

(VIII)

in which:
- R²⁰ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl; and
- R²¹, R²² and R²³ may be the same or different and may be a hydrogen atom, a halogen atom, a cyano group, a $C_1$-$C_4$-alkyl, a $C_1$-$C_4$-halogenoalkyl having 1 to 5 halogen atoms or a $C_1$-$C_4$-alkylcarbonyl.

Het represents a heterocycle of the general formula (IX)

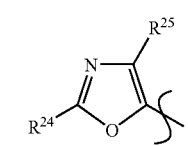

(IX)

in which:
- R²⁴ may be a hydrogen atom or a $C_1$-$C_4$-alkyl; and
- R²⁵ may be a halogen atom, a $C_1$-$C_4$-alkyl or a $C_1$-$C_4$-halogenoalkyl having 1 to 5 halogen atoms.

Het represents a heterocycle of the general formula (X)

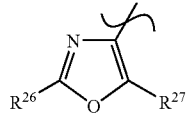
(X)

in which:
$R^{26}$ may be a hydrogen atom or a $C_1$-$C_4$-alkyl; and
$R^{27}$ may be a halogen atom, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl.

Het represents a heterocycle of the general formula (XI)

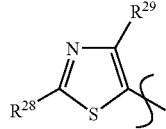
(XI)

in which:
$R^{28}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl; and
$R^{29}$ may be a halogen atom, a $C_1$-$C_4$-alkyl or a $C_1$-$C_4$-halogenoalkyl having 1 to 5 halogen atoms.

Het represents a heterocycle of the general formula (XII)

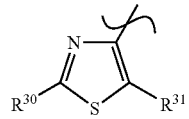
(XII)

in which:
$R^{30}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl or a $C_1$-$C_4$-halogenoalkyl having 1 to 5 halogen atoms; and
$R^{31}$ may be a halogen atom, a $C_1$-$C_4$-alkyl or a $C_1$-$C_4$-halogenoalkyl having 1 to 5 halogen atoms.

Het represents a heterocycle of the general formula (XIII)

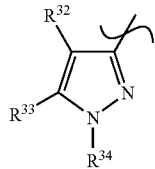
(XIII)

in which:
$R^{32}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl group or an aminocarbonyl-$C_1$-$C_4$-alkyl;
$R^{33}$ may be a hydrogen atom, a halogen atom, a cyano group, a nitro group, a $C_1$-$C_4$-alkyl, a $C_1$-$C_4$-alkoxy or a $C_1$-$C_4$-alkylthio; and
$R^{34}$ may be a hydrogen atom, a phenyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_{1\text{-}c4}$-halogenoalkylthio-$C_1$-$C_4$-alkyl having 1 to 5 halogen atoms, a $C_1$-$C_4$-alkoxy-$C_1$-$C_4$-alkyl or a $C_1$-$C_4$-halogenoalkoxy-$C_1$-$C_4$-alkyl having 1 to 5 halogen atoms.

Het represents a heterocycle of the general formula (XIV)

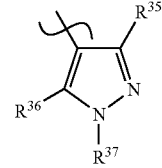
(XIV)

in which:
$R^{35}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl or an aminocarbonyl-$C_1$-$C_4$-alkyl;
$R^{36}$ may be a hydrogen atom, a halogen atom, a cyano group, a $C_1$-$C_4$-alkyl, a $C_1$-$C_4$-alkoxy, a $C_1$-$C_4$-halogenoalkoxy having 1 to 5 halogen atoms or a $C_1$-$C_4$-alkylthio; and
$R^{37}$ may be a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms or a phenyl optionally substituted by a halogen atom, a $C_1$-$C_4$-alkyl, a $C_1$-$C_4$-alkoxyalkyl or a nitro group.

Het represents a heterocycle of the general formula (XV)

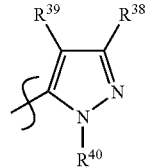
(XV)

in which:
$R^{38}$ may be a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, or an aminocarbonyl-$C_1$-$C_4$-alkyl;

$R^{39}$ may be a hydrogen atom, a halogen atom, a cyano group, a $C_1$-$C_4$-alkyl, a $C_1$-$C_4$-alkoxy, a $C_1$-$C_4$-alkylthio or a $C_1$-$C_4$-halogenoalky having 1 to 5 halogen atoms;

$R^{40}$ may be a hydrogen atom, a phenyl, a benzyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms.

Het represents a heterocycle of the general formula (XVI)

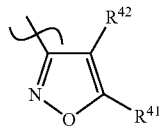

(XVI)

in which $R^{41}$ and $R^{42}$ may be the same or different and may be a hydrogen atom, a halogen atom, a $C_1$-$C_4$-alkyl or a $C_1$-$C_4$-halogenoalkyl having 1 to 5 halogen atoms.

Het represents a heterocycle of the general formula (XVII)

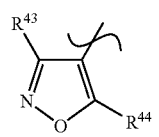

(XVII)

in which $R^{43}$ and $R^{44}$ may be the same or different and may be a hydrogen atom, a halogen atom, a $C_1$-$C_4$-alkyl, a $C_1$-$C_4$-halogenoalkyl having 1 to 5 halogen atoms, a phenyl optionally substituted by a halogen atom or a $C_1$-$C_4$-alkyl, or a heterocyclyl optionally substituted by a halogen atom or a $C_1$-$C_4$-alkyl.

Het represents a heterocycle of the general formula (XVIII)

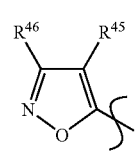

(XVIII)

in which $R^{45}$ and $R^{46}$ may be the same or different and may be a hydrogen atom, a halogen atom, a $C_1$-$C_4$-alkyl or a $C_1$-$C_4$-halogenoalkyl having 1 to 5 halogen atoms.

Het represents a heterocycle of the general formula (XIX)

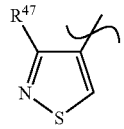

(XIX)

in which $R^{47}$ may be a halogen atom, a $C_1$-$C_4$-alkyl or a $C_1$-$C_4$-halogenoalkyl having 1 to 5 halogen atoms.

Het represents a heterocycle of the general formula (XX)

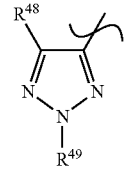

(XX)

in which:

$R^{48}$ may be a halogen atom, a $C_1$-$C_4$-alkyl or a $C_1$-$C_4$-halogenoalkyl having 1 to 5 halogen atoms; and $R^{49}$ may be a hydrogen atom, a $C_1$-$C_4$-alkyl, a $C_1$-$C_4$-halogenoalkyl having 1 to 5 halogen atoms, or a phenyl optionally substituted by a halogen atom or a $C_1$-$C_4$-alkyl.

Het represents a heterocycle of the general formula (XXI)

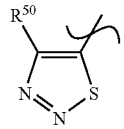

(XXI)

in which $R^{50}$ may be a halogen atom, a $C_1$-$C_4$-alkyl or a $C_1$-$C_4$-halogenoalkyl having 1 to 5 halogen atoms.

According to the present invention, "Het" of the compound of general formula (I) may be a six membered ring non-fused heterocycle. Specific examples of compounds of the present invention where Het is a six membered heterocycle include:

Het represents a heterocycle of the general formula (XXII)

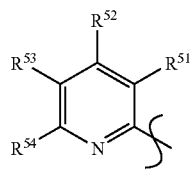

(XXII)

in which:

$R^{51}$ may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-akylthio, a $C_1$-$C_4$-halogenoalkylthio having 1 to 5 halogen atoms or a $C_1$-$C_4$-halogenoalkoxy having 1 to 5 halogen atoms;

$R^{52}$, $R^{53}$ and $R^{54}$, which may be the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl.

Het represents a heterocycle of the general formula (XXIII)

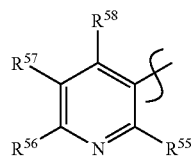

(XXIII)

in which:

$R^{55}$ may be a hydrogen atom, a halogen atom, a hydroxy group, a cyano group, an amino group, a $C_1$-$C_4$-alkyl, a $C_1$-$C_4$-halogenoalkyl having 1 to 5 halogen atoms, a $C_1$-$C_4$-alkoxy, a $C_1$-$C_5$-alkylthio, a $C_2$-$C_5$-alkenylthio a $C_1$-$C_4$-halogenoalkylthio having 1 to 5 halogen atoms, a $C_1$-$C_4$-halogenoalkoxy having 1 to 5 halogen atoms, a phenyloxy optionally substituted by a halogen atom or a $C_1$-$C_4$-alkyl, or a phenylthio optionally substituted by a halogen atom or a $C_1$-$C_4$-alkyl;

$R^{56}$, $R^{57}$ and $R^{58}$, which may the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl, a $C_1$-$C_4$-alkylsulphonyl or a N-morpholine optionally substituted by a halogen atom or a $C_1$-$C_4$-alkyl, or a thienyl optionally substituted by a halogen atom or a $C_1$-$C_4$-alkyl.

Het represents a heterocycle of the general formula (XXIV)

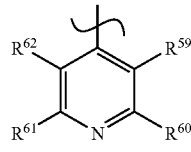

(XXIV)

in which $R^{59}$, $R^{60}$, $R^{61}$ and $R^{62}$, which may be the same or different, may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl or a $C_1$-$C_4$-alkylsulphonyl.

Het represents a heterocycle of the general formula (XXV)

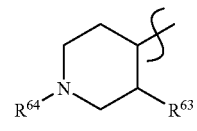

(XXV)

in which:

$R^{63}$ may be a hydrogen atom, a halogen atom, a $C_1$-$C_4$-alkyl or a $C_1$-$C_4$-halogenoalkyl having 1 to 5 halogen atoms;

$R^{64}$ may be a hydrogen atom, a $C_1$-$C_4$-alkyl, a $C_1$-$C_4$-halogenoalkyl having 1 to 5 halogen atoms, a $C_1$-$C_6$-alkoxycarbonyl, a benzyl optionally substituted by 1 to 3 halogen atoms, a benzyloxycarbonyl optionally substituted by 1 to 3 halogen atoms or a heterocyclyl.

Het represents a heterocycle of the general formula (XXVI)

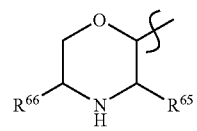

(XXVI)

in which:

$R^{65}$ may be a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms;

$R^{66}$ may be a hydrogen atom, a $C_1$-$C_4$-alkyl, a $C_1$-$C_4$-halogenoalkyl having 1 to 5 halogen atoms or a benzyl.

Het represents a heterocycle of the general formula (XXVII)

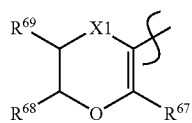

(XXVII)

in which:

$X^1$ may be a sulphur atom, —SO—, —$SO_2$— or —$CH_2$—;

$R^{67}$ may be a $C_1$-$C_4$-alkyl or a $C_1$-$C_4$-halogenoalkyl having 1 to 5 halogen atoms; and $R^{68}$ and $R^{69}$ may be the same or different and may be a hydrogen atom or a $C_1$-$C_4$-alkyl.

Het represents a heterocycle of the general formula (XXVIII)

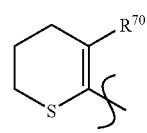

(XVIII)

in which:

$R^{70}$ may be a $C_1$-$C_4$-alkyl or a $C_1$-$C_4$-halogenoalkyl having 1 to 5 halogen atoms;

Het represents a heterocycle of the general formula (XXIX)

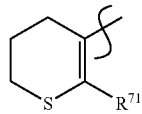
(XXIX)

in which:
R$^{71}$ may be a C$_1$-C$_4$-alkyl or a C$_1$-C$_4$-halogenoalkyl having 1 to 5 halogen atoms.

Het represents a heterocycle of the general formula (XXX)

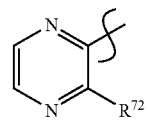
(XXX)

in which R$^{72}$ may be a hydrogen atom, a halogen atom, a C$_1$-C$_4$-alkyl or a C$_1$-C$_4$-halogenoalkyl having 1 to 5 halogen atoms.

The present invention also relates to a process for the preparation of the compound of general formula (I). Thus, according to a further aspect of the present invention there is provided a process for the preparation of compound of general formula (I) as defined above, which comprises reacting a carboxylic acid derivative of the general formula (A)

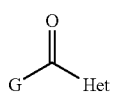
(A)

in which:
Het is as defined above;
G may be a halogen atom, a hydroxy group or a C$_1$-C$_6$-alkoxy;

with a 2-pyridine derivative of general formula (B)

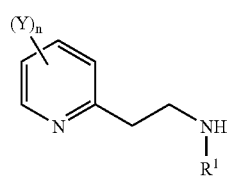
(B)

in which Y, R$^1$ and n are as defined above;

in the presence of a catalyst if G is a hydroxy or a C$_1$-C$_6$-alkoxy group, or in the presence of an acid binder if G is a halogen atom.

According to the present invention, the process for the preparation of compound of general formula (I) is carried out in the presence of a catalyst if G is a hydroxy or a C$_1$-C$_6$-alkoxy group. Suitable catalyst includes the coupling reagents dicyclohexylcarbodiimide, N,N'-carbonyldimidazole, bromotripyrrolidinophosphonium hexafluorophosphate and trimethylaluminium.

According to the present invention, the process for the preparation of compound of general formula (I) is carried out in the presence of an acid binder if G is a halogen atom. Suitable acid binder includes carbonates, aqueous alkali or tertiary amines.

The present invention also relates to another process for the preparation of the compound of general formula (I). Thus, according to a further aspect of the present invention there is provided a second process for the preparation of compound of general formula (I) as defined above, which comprises reacting a carboxylic acid anhydride derivative of general formula (C)

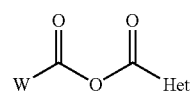
(C)

in which:
Het is as defined above;
W maybe defined as Het or a C$_1$-C$_6$-alkyl;

with a 2-pyridine derivative of the formula (D)

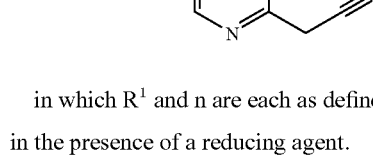
(D)

in which R$^1$ and n are each as defined above;
in the presence of a reducing agent.

According to the present invention, the second process for the preparation of compound of general formula (I) is carried out in the presence of a reducing agent. Suitable reducing agent includes H$_2$ and NaBH$_4$.

The compound according to the present invention can be prepared according to the general processes of preparation described above. It will nevertheless be understood that the skilled worker will be able to adapt this method according to the specifics of each of the compounds, which it is desired to synthesise. For example, the above mentioned processes may be carried out in the presence of a diluent if appropriate. If appropriate, the second process for the preparation of compound of general formula (I) may also be carried out in the presence of a catalyst such as NiCl$_2$—H$_2$O or CoCl$_3$—H$_2$O.

Certain of the intermediate compounds used for the preparation of compound of general formula (I) are novel. Therefore, the present invention also relates to novel intermediate compound useful for the preparation of compound of general formula (I). Thus, according to the present invention, there is provided a novel compound of general formula (E):

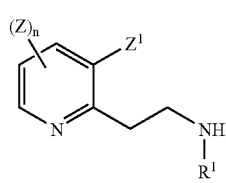
(E)

in which:

Z may be the same or different and may be a halogen atom, a nitro group, a cyano group, a hydroxy, a carboxyl group, a $C_1$-$C_8$-alkyl, a $C_1$-$C_6$-halogenoalkyl having 1 to 5 halogen atoms, a $C_1$-$C_6$-halogenoalkoxy having 1 to 5 halogen atoms, a $C_1$-$C_8$-alkylthio, a $C_1$-$C_6$-halogenoalkylthio having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkinyloxy, a $C_3$-$C_8$-halogenoalkinyloxy having 1 to 5 halogen atoms, a $C_3$-$C_8$-cycloalkyl, a $C_1$-$C_8$-alkoxycarbonyl, a $C_1$-$C_8$-alkylsulphinyl, a $C_1$-$C_8$-alkylsulphonyl, a $C_1$-$C_8$-halogenoalkylsulphinyl having 1 to 5 halogen atoms, a $C_1$-$C_8$-halogenoalkyl-sulphonyl having 1 to 5 halogen atoms or a $C_1$-$C_6$-alkoximino-$C_1$-$C_6$-alkyl;

$Z^1$ may be a halogen atom or a $C_1$-$C_8$-alkyl;

$R^1$ and n are as defined above.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be between 5% and 40% by weight.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, bait (ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers and rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants targeted by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants targeted by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis forma* specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cocliliobolus sativus*), powdery mildew (*Erysiphe graminis forma* specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops for example rape, as regards controlling the following seed diseases: *Phoma lingam, Alternaria brassicae* and *Sclerotinia sclerotiorum;* corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active material applied is generally and advantageously between 2 and 200 g per 100 kg of seed, preferably between 3 and 150 g per 100 kg of seed in the case of seed treatments. It is clearly understood that the doses indicated above are given as illustrative examples of the invention. A person skilled in the art will know how to tailor the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used to curatively or preventively treat human and animal fungal diseases such as, for example, mycoses, dermatoses, trichophyton diseases and candidiases or diseases caused by *Aspergillus* spp., for example *Aspergillus fumigatus*.

The aspects of the present invention will now be illustrated with reference to the following tables of compounds and examples. The following Tables A to V illustrate in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy and M (ApcI+) means the molecular ion peak as it was found via positive atmospheric pressure chemical ionisation in mass spectroscopy.

TABLE A

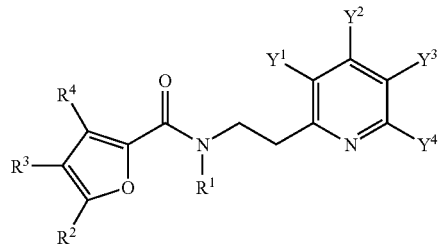

| Compound | $R^1$ | $R^2$ | $R^3$ | $R^4$ | $Y^1$ | $Y^2$ | $Y^3$ | $Y^4$ | M + 1 |
|---|---|---|---|---|---|---|---|---|---|
| A-1 | H | H | H | H | Cl | H | $CF_3$ | H | 319 at 1 $^{35}Cl$ |
| A-2 | H | $NO_2$ | H | H | Cl | H | $CF_3$ | H | 364 at 1 $^{35}Cl$ |
| A-3 | H | H | H | Me | Cl | H | $CF_3$ | H | 333 at 1 $^{35}Cl$ |
| A-4 | H | H | H | Br | Cl | H | $CF_3$ | H | 397 at 1 $^{35}Cl$ and 1 $^{79}Br$ |

TABLE B

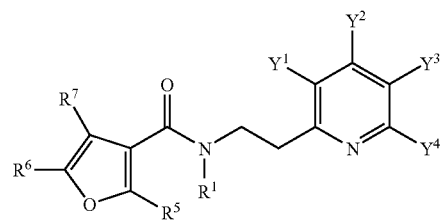

| Compound | $R^1$ | $R^5$ | $R^6$ | $R^7$ | $Y^1$ | $Y^2$ | $Y^3$ | $Y^4$ | M (ApcI+) | M + 1 |
|---|---|---|---|---|---|---|---|---|---|---|
| B-1 | H | Me | H | H | Cl | H | $CF_3$ | H | | 333 at 1 $^{35}Cl$ |
| B-2 | H | $CF_3$ | 4-chlorophenyl | H | Cl | H | $CF_3$ | H | | 497 at 2 $^{35}Cl$ |
| B-3 | H | H | H | H | Cl | H | $CF_3$ | H | | 319 at 1 $^{35}Cl$ |
| B-4 | H | Me | t-Bu | H | Cl | H | $CF_3$ | H | | 389 at 1 $^{35}Cl$ |
| B-5 | H | Me | Ph | H | Cl | H | $CF_3$ | H | | 409 at 1 $^{35}Cl$ |
| B-6 | H | Me | 4-chlorophenyl | H | Cl | H | $CF_3$ | H | | 443 at 2 $^{35}Cl$ |
| B-7 | H | Me | Me | H | Cl | H | $CF_3$ | H | | 347 at 1 $^{35}Cl$ |
| B-8 | H | $CF_3$ | Me | H | Cl | H | $CF_3$ | H | | 401 at 1 $^{35}Cl$ |
| B-9 | H | $CF_3$ | 3-chlorophenyl | H | Cl | H | $CF_3$ | H | 496 at 2 $^{35}Cl$ | |
| B-10 | H | $CF_3$ | Ph | H | Cl | H | $CF_3$ | H | | 463 at 1 $^{35}Cl$ |
| B-11 | H | H | H | Me | Cl | H | $CF_3$ | H | | 333 at 1 $^{35}Cl$ |
| B-12 | H | $CF_3$ | H | H | Cl | H | $CF_3$ | H | | 387 at 1 $^{35}Cl$ |
| B-13 | H | Me | H | H | Cl | H | Cl | H | | |
| B-14 | H | I | H | H | Cl | H | $CF_3$ | H | | 445 at 1 $^{35}Cl$ |
| B-15 | Cyclopropyl | I | H | H | Cl | H | $CF_3$ | H | | 485 at 1 $^{35}Cl$ |
| B-16 | H | Me | Me | H | Cl | H | Cl | Me | | 327 at 2 $^{35}Cl$ |
| B-17 | H | Me | Me | H | F | H | F | F | | 299 |
| B-18 | H | I | H | H | F | H | F | F | | 397 |
| B-19 | H | Me | H | H | F | H | F | F | | 285 |
| B-20 | H | Me | Me | H | F | Me | F | F | | 313 |
| B-21 | H | Me | H | H | F | Me | F | F | | 299 |
| B-22 | H | I | H | H | F | Me | F | F | | 411 |

TABLE C

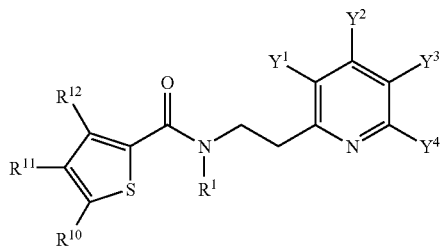

| Compound | R¹ | R¹⁰ | R¹¹ | R¹² | Y¹ | Y² | Y³ | Y⁴ | M (ApcI+) | M + 1 |
|---|---|---|---|---|---|---|---|---|---|---|
| C-1 | H | H | H | H | Cl | H | CF$_3$ | H | | 335 at 1 $^{35}$Cl |
| C-2 | H | H | H | Cl | Cl | H | CF$_3$ | H | | 369 at 2 $^{35}$Cl |
| C-3 | H | H | H | Me | Cl | H | CF$_3$ | H | | 349 at 1 $^{35}$Cl |
| C-4 | H | H | SO$_2$iPr | Cl | Cl | H | CF$_3$ | H | | 475 at 2 $^{35}$Cl |
| C-5 | H | H | H | Br | Cl | H | CF$_3$ | H | 412 at 1 $^{35}$Cl and 1 $^{79}$Br | |
| C-6 | H | 2-Pyridyl | H | H | Cl | H | CF$_3$ | H | | 412 at 1 $^{35}$Cl |
| C-7 | H | Ph | H | H | Cl | H | CF$_3$ | H | | 411 at 1 $^{35}$Cl |
| C-8 | H | H | SO$_2$Me | Cl | Cl | H | CF$_3$ | H | 446 at 1 $^{35}$Cl | |
| C-9 | H | SMe | SO$_2$iPr | Cl | Cl | H | CF$_3$ | H | | 521 at 2 $^{35}$Cl |
| C-10 | H | SMe | SO$_2$iPr | I | Cl | H | CF$_3$ | H | 612 at 1 $^{35}$Cl | |
| C-11 | H | Cl | Cl | Cl | Cl | H | CF$_3$ | H | 436 at 4 $^{35}$Cl | |
| C-12 | H | H | H | I | Cl | H | CF$_3$ | H | | 461 at 1 $^{35}$Cl |
| C-13 | H | H | H | I | Cl | H | Cl | H | | |
| C-14 | H | H | H | Me | F | H | Cl | H | | 333 at 1 $^{35}$Cl |
| C-15 | H | H | H | I | F | H | Cl | H | | 411 at 1 $^{35}$Cl |
| C-16 | H | H | H | I | Br | H | Cl | H | | 471 at 1 $^{35}$Cl and 1 $^{79}$Br |
| C-17 | H | H | H | I | H | H | Cl | H | | 393 at 1 $^{35}$Cl |
| C-18 | H | H | H | I | Cl | H | H | Cl | | 427 at 2 $^{35}$Cl |
| C-19 | H | H | H | I | H | H | Me | H | | 373 |
| C-20 | Cyclopropyl | H | H | I | Cl | H | CF$_3$ | H | | |
| C-21 | H | H | H | I | Cl | H | Cl | Me | | 441 at 2 $^{35}$Cl |
| C-22 | H | H | H | I | Cl | H | Cl | F | | 445 at 2 $^{35}$Cl |
| C-23 | H | H | H | I | F | H | Cl | F | | |
| C-24 | H | H | H | I | H | H | CF$_3$ | Cl | | 461 at 1 $^{35}$Cl |
| C-25 | H | H | H | Me | H | H | CF$_3$ | Cl | | |
| C-26 | H | H | H | Me | F | H | F | F | | 301 |
| C-27 | H | H | H | Br | F | H | F | F | | 365 at 1 $^{79}$Br |
| C-28 | H | H | H | I | F | H | F | F | | 413 |
| C-29 | H | H | H | Me | F | Me | F | F | | 315 |
| C-30 | H | H | H | Br | F | Me | F | F | | 379 at 1 $^{79}$Br |
| C-31 | H | H | H | I | F | Me | F | F | | 427 |

TABLE D

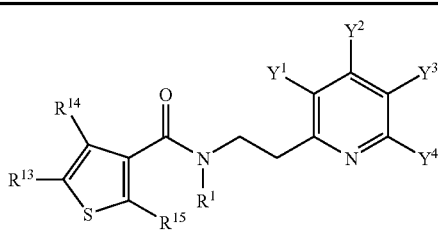

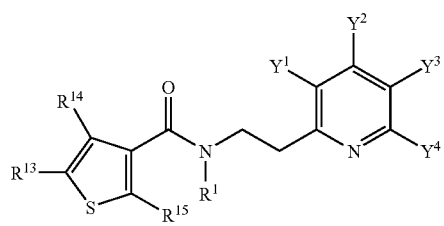

| Compound | R¹ | R¹³ | R¹⁴ | R¹⁵ | Y¹ | Y² | Y³ | Y⁴ | M + 1 |
|---|---|---|---|---|---|---|---|---|---|
| D-1 | H | Cl | OMe | H | Cl | H | CF$_3$ | H | 399 at 2 $^{35}$Cl |
| D-2 | H | H | H | H | Cl | H | CF$_3$ | H | 335 at 1 $^{35}$Cl |
| D-3 | H | H | Me | H | Cl | H | CF$_3$ | H | 349 at 1 $^{35}$Cl |
| D-4 | H | H | H | I | Cl | H | CF$_3$ | H | 461 at 1 $^{35}$Cl |
| D-5 | H | H | Me | H | Cl | H | CF$_3$ | H | 349 at 1 $^{35}$Cl |
| D-6 | H | H | H | I | F | H | F | F | 413 at 1 $^{35}$Cl |
| D-7 | H | H | H | I | F | Me | F | F | 427 at 1 $^{35}$Cl |

TABLE E

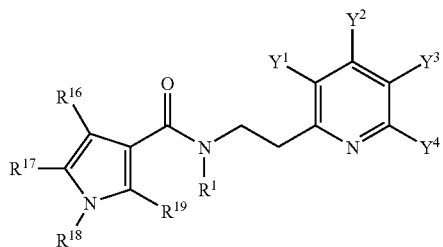

| Compound | R¹ | R¹⁶ | R¹⁷ | R¹⁸ | R¹⁹ | Y¹ | Y² | Y³ | Y⁴ | M + 1 | M − 1 |
|---|---|---|---|---|---|---|---|---|---|---|---|
| E-1 | H | H | Me | Me | Me | Cl | H | CF₃ | H | | 358 at 1 ³⁵Cl |
| E-2 | H | CF₃ | Me | Me | H | Cl | H | CF₃ | H | 400 at 1 ³⁵Cl | |
| E-3 | H | CF₃ | H | Me | H | Cl | H | F | F | 352 | |
| E-4 | H | CF₃ | H | Me | H | Cl | Me | F | F | 366 | |

TABLE F

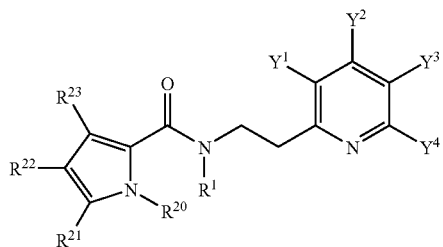

| Compound | R¹ | R²⁰ | R²¹ | R²² | R²³ | Y¹ | Y² | Y³ | Y⁴ | M (APcI+) | M + 1 |
|---|---|---|---|---|---|---|---|---|---|---|---|
| F-1 | H | Me | H | H | H | Cl | H | CF₃ | H | | 332 at 1 ³⁵Cl |
| F-2 | H | H | Me | Ac | Me | Cl | H | CF₃ | H | 387 at 1 ³⁵Cl | |
| F-3 | H | Me | H | H | I | Cl | H | CF₃ | H | | 458 at 1 ³⁵Cl |

TABLE G

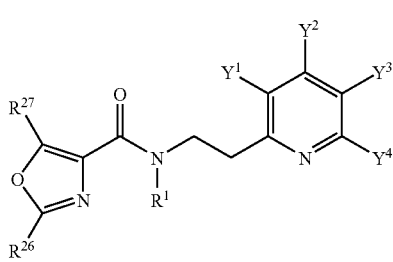

| Compound | R¹ | R²⁶ | R²⁷ | Y¹ | Y² | Y³ | Y⁴ | M + 1 |
|---|---|---|---|---|---|---|---|---|
| G-1 | H | H | Ph | Cl | H | CF₃ | H | 396 at 1 ³⁵Cl |
| G-2 | H | Me | CF₃ | Cl | H | CF₃ | H | 402 at 1 ³⁵Cl |

TABLE H

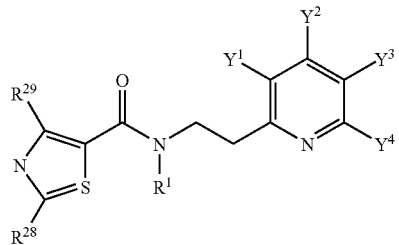

| Compound | R¹ | R²⁸ | R²⁹ | Y¹ | Y² | Y³ | Y⁴ | M + 1 |
|---|---|---|---|---|---|---|---|---|
| H-1 | H | Me | CF₃ | Cl | H | CF₃ | H | 418 at 1 ³⁵Cl |
| H-2 | H | Me | CHF₂ | Cl | H | CF₃ | H | 400 at 1 ³⁵Cl |
| H-3 | H | Ph | Me | Cl | H | CF₃ | H | 426 at 1 ³⁵Cl |
| H-4 | H | Me | CF₃ | Cl | H | Cl | H | |
| H-5 | H | Me | CF₃ | Cl | H | H | Cl | 384 at 2 ³⁵Cl |
| H-6 | H | Me | CF₃ | Cl | H | Methoxy-iminoethyl | H | 407 at 1 ³⁵Cl |

TABLE H-continued

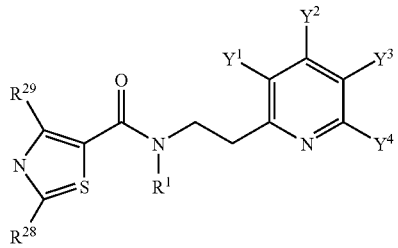

| Compound | R¹ | R²⁸ | R²⁹ | Y¹ | Y² | Y³ | Y⁴ | M + 1 |
|---|---|---|---|---|---|---|---|---|
| H-7 | H | Me | CF₃ | Cl | H | Ethoxy-iminomethyl | H | 421 at 1 ³⁵Cl |
| H-8 | H | Me | CF₃ | Cl | H | Isopropox-iminoethyl | H | 435 at 1 ³⁵Cl |
| H-9 | H | Me | CF₃ | Cl | H | Cl | Cl | 418 at 3 ³⁵Cl |
| H-10 | H | Me | CF₃ | F | H | Cl | H | 368 at 1 ³⁵Cl |
| H-11 | Cyclopropyl | Me | CF₃ | Cl | H | CF₃ | H | 458 at 1 ³⁵Cl |
| H-12 | H | Me | CF₃ | F | Me | F | F | 384 |
| H-13 | H | Me | CF₃ | Cl | H | Cl | Me | 398 at 2 ³⁵Cl |
| H-14 | H | Me | CF₃ | F | H | F | F | 370 |

TABLE H-continued

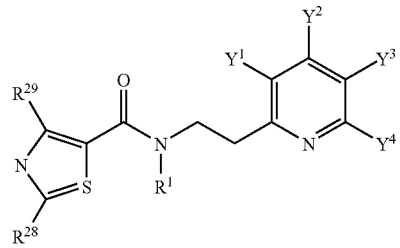

| Compound | R¹ | R²⁸ | R²⁹ | Y¹ | Y² | Y³ | Y⁴ | M + 1 |
|---|---|---|---|---|---|---|---|---|
| H-15 | Cyclopropyl | Me | CHF₂ | Cl | H | CF₃ | H | 440 at 1 ³⁵Cl |
| H-16 | H | Me | CHF₂ | F | Me | F | F | 366 |
| H-17 | H | Me | CHF₂ | Cl | H | Br | H | 409 at 1 ³⁵Cl and 1 ⁷⁹Br |
| H-18 | H | Me | CHF₂ | Br | H | CF₃ | H | 444 at 1 ⁷⁹Br |
| H-19 | H | Me | CHF₂ | Cl | H | Cl | Me | 380 at 2 ³⁵Cl |
| H-20 | H | Me | CHF₂ | Cl | H | Cl | F | 384 at 2 ³⁵Cl |
| H-21 | H | Me | CHF₂ | F | H | F | F | 352 |
| H-22 | H | Me | CHF₂ | F | H | Cl | F | 368 at 1 ³⁵Cl |
| H-23 | H | Me | CHF₂ | H | H | CF₃ | Cl | 400 at 1 ³⁵Cl |

TABLE I

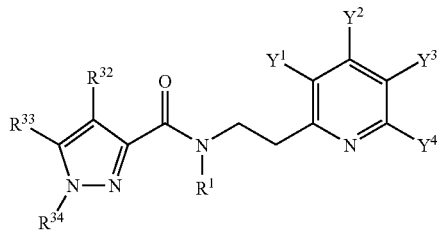

| Compound | R¹ | R³² | R³³ | R³⁴ | Y¹ | Y² | Y³ | Y⁴ | M (APcI+) | M + 1 |
|---|---|---|---|---|---|---|---|---|---|---|
| I-1 | H | H | Me | t-Bu | Cl | H | CF₃ | H | | 389 at 1 ³⁵Cl |
| I-2 | H | H | Me | Me | Cl | H | CF₃ | H | | 347 at 1 ³⁵Cl |
| I-3 | H | Br | NO₂ | Me | Cl | H | CF₃ | H | 455 at 1 ³⁵Cl and 1 ⁷⁹Br | |
| I-4 | H | I | H | Me | Cl | H | CF₃ | H | | 459 at 1³⁵Cl |

TABLE J

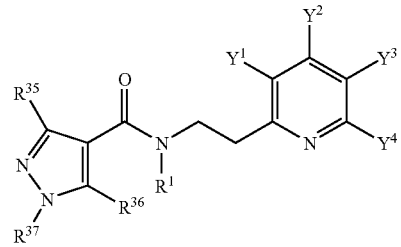

| Compound | R¹ | R³⁵ | R³⁶ | R³⁷ | Y¹ | Y² | Y³ | Y⁴ | M + 1 |
|---|---|---|---|---|---|---|---|---|---|
| J-1 | H | Me | F | Me | Cl | H | CF₃ | H | 365 at 1 ³⁵Cl |
| J-2 | H | Me | H | Me | Cl | H | CF₃ | H | 347 at 1 ³⁵Cl |
| J-3 | H | CHF₂ | H | Me | Cl | H | CF₃ | H | 383 at 1 ³⁵Cl |
| J-4 | H | H | CF₃ | Ph | Cl | H | CF₃ | H | 463 at 1 ³⁵Cl |
| J-5 | H | H | CF₃ | 4-chlorophenyl | Cl | H | CF₃ | H | 497 at 2 ³⁵Cl |
| J-6 | H | H | Cl | Me | Cl | H | CF₃ | H | 367 at 2 ³⁵Cl |
| J-7 | H | H | Me | 4-fluorophenyl | Cl | H | CF₃ | H | 427 at 1 ³⁵Cl |
| J-8 | H | H | Me | 4-methoxyphenyl | Cl | H | CF₃ | H | 439 at 1 ³⁵Cl |

TABLE J-continued

| Compound | R¹ | R³⁵ | R³⁶ | R³⁷ | Y¹ | Y² | Y³ | Y⁴ | M + 1 |
|---|---|---|---|---|---|---|---|---|---|
| J-9 | H | H | Me | Ph | Cl | H | CF$_3$ | H | 409 at 1 $^{35}$Cl |
| J-10 | H | H | Me | 2-methylphenyl | Cl | H | CF$_3$ | H | 423 at 1 $^{35}$Cl |
| J-11 | H | H | n-Pr | Ph | Cl | H | CF$_3$ | H | 437 at 1 $^{35}$Cl |
| J-12 | H | H | n-Pr | 4-chlorophenyl | Cl | H | CF$_3$ | H | 471 at 2 $^{35}$Cl |
| J-13 | H | H | CF$_3$ | 4-nitrophenyl | Cl | H | CF$_3$ | H | 508 at 1 $^{35}$Cl |
| J-14 | H | Me | Me | Me | Cl | H | CF$_3$ | H | 361 at 1 $^{35}$Cl |
| J-15 | H | Cl | H | Me | Cl | H | CF$_3$ | H | 367 at 2 $^{35}$Cl |
| J-16 | H | I | H | Me | Cl | H | CF$_3$ | H | 459 at 1 $^{35}$Cl |
| J-17 | H | Me | Me | Me | Cl | H | Cl | H | |
| J-18 | H | Me | F | Me | Cl | H | Cl | H | 330 at 2 $^{35}$Cl |
| J-19 | H | Me | H | Me | Cl | H | Cl | H | |
| J-20 | H | CF$_3$ | H | Me | Cl | H | Cl | Cl | 401 at 3 $^{35}$Cl |
| J-21 | H | CF$_3$ | H | Me | F | H | Cl | H | 351 at 1 $^{35}$Cl |
| J-22 | H | CF$_3$ | H | Me | Cl | H | H | Cl | 365 at 2 $^{35}$Cl |
| J-23 | Cyclopropyl | CF$_3$ | H | Me | Cl | H | CF$_3$ | H | 441 at 1 $^{35}$Cl |
| J-24 | H | CF$_3$ | H | Me | H | H | CF$_3$ | Cl | 401 at 1 $^{35}$Cl |
| J-25 | H | CF$_3$ | H | Me | Cl | H | Cl | Me | 381 at 2 $^{35}$Cl |
| J-26 | H | CF$_3$ | H | Me | Cl | H | Cl | F | 385 at 2 $^{35}$Cl |
| J-27 | H | CF$_3$ | H | Me | F | H | F | F | 353 |
| J-28 | H | CF$_3$ | H | Me | F | Me | F | F | 367 |
| J-29 | H | CHF$_2$ | H | Me | Cl | H | Cl | H | |
| J-30 | H | CHF$_2$ | H | Me | H | H | Me | H | 295 |
| J-31 | H | CHF$_2$ | H | Me | H | H | Methoximinoethyl | H | 386 at 1 $^{35}$Cl |
| J-32 | H | CHF$_2$ | H | Me | Me | H | Br | H | |
| J-33 | H | CHF$_2$ | H | Me | F | H | Cl | H | 333 at 1 $^{35}$Cl |
| J-34 | H | CHF$_2$ | H | Me | Cl | H | Cl | Cl | 383 at 3 $^{35}$Cl |
| J-35 | H | CHF$_2$ | H | Me | Cl | H | Methoximinoethyl | H | 372 at 1 $^{35}$Cl |
| J-36 | H | CHF$_2$ | H | Me | H | H | Cl | H | |
| J-37 | H | CHF$_2$ | H | Me | Cl | H | Ethoximinoethyl | H | 386 at 1 $^{35}$Cl |
| J-38 | H | CHF$_2$ | H | Me | Cl | H | Isopropoxyiminoethyl | H | |
| J-39 | H | CHF$_2$ | H | Me | Br | H | Cl | H | 393 at 1 $^{35}$Cl and 1 $^{79}$Br |
| J-40 | H | CHF$_2$ | H | Me | F | Me | F | F | 349 |
| J-41 | Cyclopropyl | CHF$_2$ | H | Me | Cl | H | CF$_3$ | | 423 at 1 $^{35}$Cl |
| J-42 | H | CHF$_2$ | H | Me | H | H | CF$_3$ | | 383 at 1 $^{35}$Cl |
| J-43 | H | CHF$_2$ | H | Me | Cl | H | Br | | |
| J-44 | H | CHF$_2$ | H | Me | F | H | Cl | | 351 at 1 $^{35}$Cl |
| J-45 | H | CHF$_2$ | H | Me | Br | H | CF$_3$ | | 417 at 1 $^{79}$Br |
| J-46 | H | Me | F | Me | Cl | H | Cl | | |
| J-47 | H | Me | F | Me | H | H | Me | | 277 |
| J-48 | H | Me | F | Me | Cl | H | Methoximinoethyl | H | |
| J-49 | H | Me | F | Me | F | H | Cl | H | 315 at 1 $^{35}$Cl |
| J-50 | H | Me | F | Me | Cl | H | Cl | Cl | 365 at 3 $^{35}$Cl |
| J-51 | H | Me | F | Me | Cl | H | Methoximinoethyl | H | 354 at 1 $^{35}$Cl |
| J-52 | Cyclopropyl | Me | F | Me | Cl | H | CF$_3$ | H | 405 at 1 $^{35}$Cl |
| J-53 | H | Me | F | Me | F | H | F | H | 317 |
| J-54 | H | CF$_3$ | H | Me | Cl | H | CF$_3$ | H | |
| J-55 | H | Fluorethyl | H | Me | Cl | H | CF$_3$ | H | |
| J-56 | H | Formyl | H | Me | Cl | H | CF$_3$ | H | |
| J-57 | H | Cl | H | Me | Cl | H | CF$_3$ | H | |
| J-58 | H | I | H | Me | Cl | H | CF$_3$ | H | |
| J-59 | H | Me | H | Me | Cl | H | CF$_3$ | H | |
| J-60 | H | CHCl$_2$ | H | Me | Cl | H | CF$_3$ | H | |
| J-61 | H | H | Fluorethyl | Me | Cl | H | CF$_3$ | H | |

TABLE K

| Compound | R¹ | R³⁸ | R³⁹ | R⁴⁰ | Y¹ | Y² | Y³ | Y⁴ | M + 1 |
|---|---|---|---|---|---|---|---|---|---|
| K-1 | H | Me | H | t-Bu | Cl | H | CF₃ | H | 389 at 1 ³⁵Cl |
| K-2 | H | t-Bu | H | Me | Cl | H | CF₃ | H | 334 at 1 ³⁵Cl |
| K-3 | H | t-Bu | H | Benzyl | Cl | H | CF₃ | H | 465 at 1 ³⁵Cl |
| K-4 | H | Me | H | Me | Cl | H | CF₃ | H | 347 at 1 ³⁵Cl |
| K-5 | H | H | H | Ph | Cl | H | CF₃ | H | 395 at 1 ³⁵Cl |
| K-6 | H | Me | Br | Et | Cl | H | CF₃ | H | 439 at 1 ³⁵Cl and 1 ⁷⁹Br |

TABLE L

| Compound | R¹ | R⁴¹ | R⁴² | Y¹ | Y² | Y³ | Y⁴ | M + 1 |
|---|---|---|---|---|---|---|---|---|
| L-1 | H | Me | H | Cl | H | CF₃ | H | 394 at 1 ³⁵Cl |

TABLE M

| Compound | R¹ | R⁴³ | R⁴⁴ | Y¹ | Y² | Y³ | Y⁴ | M − 1 | M + 1 |
|---|---|---|---|---|---|---|---|---|---|
| M-1 | H | Me | 4-methyl-[1,2,3]thiadiazol-5-yl | Cl | H | CF₃ | H | | 432 at 1 ³⁵Cl |
| M-2 | H | Me | Me | Cl | H | CF₃ | H | | 348 at 1 ³⁵Cl |
| M-3 | H | Ph | Me | Cl | H | CF₃ | H | 408 at 1 ³⁵Cl | |
| M-4 | H | 2-chlorophenyl | Me | Cl | H | CF₃ | H | | 444 at 2 ³⁵Cl |
| M-5 | H | 2,6-dichlorophenyl | Me | Cl | H | CF₃ | H | | 478 at 3 ³⁵Cl |
| M-6 | H | 2-chloro-6-fluorophenyl | Me | Cl | H | CF₃ | H | | 462 at 2 ³⁵Cl |
| M-7 | H | 4-chlorophenyl | Me | Cl | H | CF₃ | H | | 444 at 1 ³⁵Cl |

TABLE N

| Compound | R¹ | R⁴⁵ | R⁴⁶ | Y¹ | Y² | Y³ | Y⁴ | M + 1 |
|---|---|---|---|---|---|---|---|---|
| N-1 | H | H | H | Cl | H | CF₃ | H | 320 at 1 ³⁵Cl |

TABLE O

| Compound | R¹ | R⁴⁸ | R⁴⁹ | Y¹ | Y² | Y³ | Y⁴ | M + 1 |
|---|---|---|---|---|---|---|---|---|
| O-1 | H | Me | Ph | Cl | H | CF₃ | H | 410 at 1 ³⁵Cl |

TABLE P

| Compound | R¹ | R⁵⁰ | R⁴⁹ | Y¹ | Y² | Y³ | Y⁴ | M + 1 |
|---|---|---|---|---|---|---|---|---|
| P-1 | H | Me | Cl | Cl | H | CF₃ | H | 351 at 1 ³⁵Cl |

TABLE Q

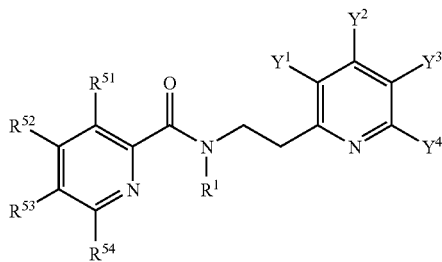

| Compound | R¹ | R⁵¹ | R⁵² | R⁵³ | R⁵⁴ | Y¹ | Y² | Y³ | Y⁴ | M (APcI+) | M + 1 |
|---|---|---|---|---|---|---|---|---|---|---|---|
| Q-1 | H | Cl | H | $CF_3$ | H | Cl | H | $CF_3$ | H | | 432 at 2 $^{35}Cl$ |
| Q-2 | H | Cl | H | H | Cl | Cl | H | $CF_3$ | H | 397 at 3 $^{35}Cl$ | |
| Q-3 | H | Me | H | H | H | Cl | H | $CF_3$ | H | | 344 at 1 $^{35}Cl$ |

TABLE R

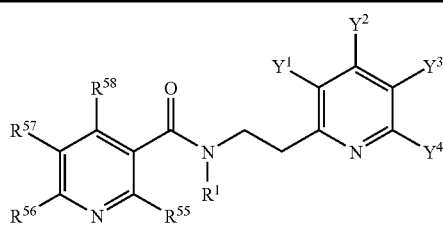

| Compound | R¹ | R⁵⁵ | R⁵⁶ | R⁵⁷ | R⁵⁸ | Y¹ | Y² | Y³ | Y⁴ | M (ApcI+) | M + 1 |
|---|---|---|---|---|---|---|---|---|---|---|---|
| R-1 | H | Cl | H | H | H | Cl | H | $CF_3$ | H | | 364 at 2 $^{35}Cl$ |
| R-2 | H | Cl | H | H | H | Cl | H | Cl | H | | |
| R-3 | H | SEt | H | H | H | Cl | H | $CF_3$ | H | | 390 at 1 $^{35}Cl$ |
| R-4 | H | H | Cl | H | H | Cl | H | $CF_3$ | H | | 364 at 2 $^{35}Cl$ |
| R-5 | H | H | H | H | H | Cl | H | $CF_3$ | H | | 330 at 1 $^{35}Cl$ |
| R-6 | H | SPh | H | H | H | Cl | H | $CF_3$ | H | | 438 at 1 $^{35}Cl$ |
| R-7 | H | 4-chlorophenoxy | H | H | H | Cl | H | $CF_3$ | H | | 456 at 2 $^{35}Cl$ |
| R-8 | H | H | H | 2-Thienyl | H | Cl | H | $CF_3$ | H | | 412 at 1 $^{35}Cl$ |
| R-9 | H | H | N-Morpholino | H | H | Cl | H | $CF_3$ | H | | 415 at 1 $^{35}Cl$ |
| R-10 | H | Me | H | H | H | Cl | H | $CF_3$ | H | | 344 at 1 $^{35}Cl$ |
| R-11 | H | 3-propenyl-sulfinyl | H | H | H | Cl | H | $CF_3$ | H | | 402 at 1 $^{35}Cl$ |
| R-12 | H | SnPr | H | H | H | Cl | H | $CF_3$ | H | | 404 at 1 $^{35}Cl$ |
| R-13 | H | n-pentylsulfinyl | H | H | H | Cl | H | $CF_3$ | H | | 432 at 1 $^{35}Cl$ |
| R-14 | H | Cl | Cl | F | H | Cl | H | $CF_3$ | H | | 415 at 3 $^{35}Cl$ |
| R-15 | H | Me | $CF_3$ | H | H | Cl | H | $CF_3$ | H | | 412 at 1 $^{35}Cl$ |
| R-16 | H | CN | H | H | H | Cl | H | $CF_3$ | H | | 355 at 1 $^{35}Cl$ |
| R-17 | H | Cl | Me | H | H | Cl | H | $CF_3$ | H | | 378 at 2 $^{35}Cl$ |
| R-18 | H | $CF_3$ | H | H | H | Cl | H | $CF_3$ | H | | 398 at 1 $^{35}Cl$ |
| R-19 | H | F | H | H | H | Cl | H | $CF_3$ | H | | 348 at 1 $^{35}Cl$ |
| R-20 | H | H | H | H | $CF_3$ | Cl | H | $CF_3$ | H | | 398 at 1 $^{35}Cl$ |
| R-21 | H | Cl | Cl | H | H | Cl | H | $CF_3$ | H | 397 at 3 $^{35}Cl$ | 398 at 3 $^{35}Cl$ |
| R-22 | H | Cl | H | Cl | H | Cl | H | $CF_3$ | H | 397 at 3 $^{35}Cl$ | 398 at 3 $^{35}Cl$ |
| R-23 | H | Cl | H | H | H | Cl | H | 1-methoximinoethyl | H | | 367 at 2 $^{35}Cl$ |
| R-24 | H | Cl | H | H | H | F | H | Cl | H | | 314 at 2 $^{35}Cl$ |
| R-25 | H | $NH_2$ | H | H | H | Cl | H | $CF_3$ | H | | 345 at 1 $^{35}Cl$ |
| R-26 | H | Br | H | H | H | Cl | H | $CF_3$ | H | | 408 at 1 $^{35}Cl$ and 1 $^{79}Br$ |
| R-27 | H | H | H | H | H | Cl | H | $CF_3$ | H | | 456 at 1 $^{35}Cl$ |
| R-28 | H | SH | H | H | H | Cl | H | $CF_3$ | H | | 362 at 1 $^{35}Cl$ |
| R-29 | H | Cl | H | H | H | Cl | H | Cl | H | | 364 at 4 $^{35}Cl$ |
| R-30 | H | Cl | H | H | H | Cl | H | Methoximinoethyl | H | | 353 at 2 $^{35}Cl$ |
| R-31 | H | Cl | H | H | H | Cl | H | Ethoximinoethyl | H | | 367 at 2 $^{35}Cl$ |
| R-32 | H | H | H | H | H | H | H | Cl | H | | 296 at 2 $^{35}Cl$ |
| R-33 | Cyclopropyl | Cl | Me | H | H | Cl | H | $CF_3$ | H | | 418 at 2 $^{35}Cl$ |
| R-37 | H | Cl | Cl | H | H | $CF_3$ | Cl | H | $CF_3$ | H | 466 at 3 $^{35}Cl$ |
| R-35 | H | Cl | Me | H | H | F | Me | F | F | | 344 at 1 $^{35}Cl$ |
| R-36 | H | Cl | Me | H | H | F | H | F | F | | 330 at 1 $^{35}Cl$ |

TABLE S

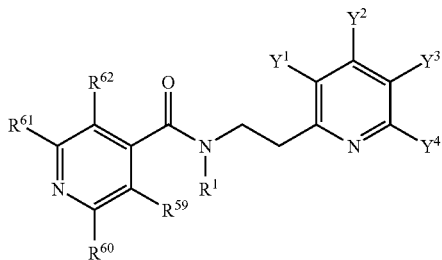

| Compound | R$^1$ | R$^{59}$ | R$^{60}$ | R$^{61}$ | R$^{62}$ | Y$^1$ | Y$^2$ | Y$^3$ | Y$^4$ | M + 1 |
|---|---|---|---|---|---|---|---|---|---|---|
| S-1 | H | H | Cl | Cl | H | Cl | H | CF$_3$ | H | 398 at 3 $^{35}$Cl |
| S-2 | H | H | Me | Cl | H | Cl | H | CF$_3$ | H | 378 at 2 $^{35}$Cl |
| S-3 | H | H | OMe | Cl | H | Cl | H | CF$_3$ | H | 330 at 2 $^{35}$Cl |
| S-4 | H | H | H | H | H | Cl | H | CF$_3$ | H | 330 at 1 $^{35}$Cl |
| S-5 | H | H | H | Cl | H | Cl | H | CF$_3$ | H | 364 at 2 $^{35}$Cl |
| S-6 | H | NH$_2$ | H | H | H | Cl | H | CF$_3$ | H | 345 at 1 $^{35}$Cl |
| S-7 | H | I | H | H | H | Cl | H | CF$_3$ | H | 456 at 1 $^{35}$Cl |
| S-8 | H | Br | H | H | H | Cl | H | CF$_3$ | H | 408 at 1 $^{35}$Cl and 1 $^{79}$Br |

TABLE T

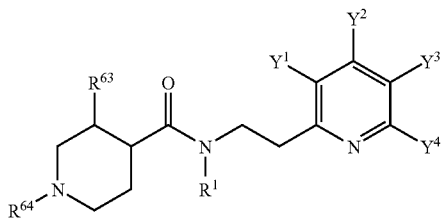

| Compound | R$^1$ | R$^{63}$ | R$^{64}$ | Y$^1$ | Y$^2$ | Y$^3$ | Y$^4$ | M + 1 |
|---|---|---|---|---|---|---|---|---|
| T-1 | H | H | Benzyloxycarbonyl | Cl | H | CF$_3$ | H | 470 at 1 $^{35}$Cl |
| T-2 | H | H | 4-trifluormethyl-pyrimidin-2-yl | Cl | H | CF$_3$ | H | 482 at 1 $^{35}$Cl |

TABLE U

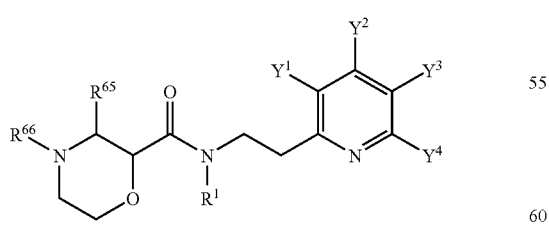

| Compound | R$^1$ | R$^{65}$ | R$^{66}$ | Y$^1$ | Y$^2$ | Y$^3$ | Y$^4$ | M + 1 |
|---|---|---|---|---|---|---|---|---|
| U-1 | H | H | Benzyl | Cl | H | CF$_3$ | H | 428 at 1 $^{35}$Cl |

TABLE V

| Compound | $R^1$ | $R^{67}$ | $R^{68}$ | $R^{69}$ | $X^1$ | $Y^1$ | $Y^2$ | $Y^3$ | $Y^4$ | M + 1 |
|---|---|---|---|---|---|---|---|---|---|---|
| V-1 | H | Me | H | H | S | Cl | H | $CF_3$ | H | 367 at 1 $^{35}Cl$ |
| V-2 | H | $CF_3$ | H | H | S | Cl | H | $CF_3$ | H | 421 at 1 $^{35}Cl$ |
| V-3 | H | $CF_3$ | Me | H | S | Cl | H | $CF_3$ | H | 435 at 1 $^{35}Cl$ |
| V-4 | H | $CF_3$ | H | Me | S | Cl | H | $CF_3$ | H | 435 at 1 $^{35}Cl$ |
| V-5 | H | $CHF_2$ | H | H | S | Cl | H | $CF_3$ | H | |
| V-6 | H | Me | H | H | S | Cl | H | Cl | H | |
| V-7 | H | Me | H | H | S | Cl | H | Cl | Cl | 521 at 3 $^{35}Cl$ |
| V-8 | H | Me | H | H | S | Cl | H | Methoximinomethyl | H | 356 at 1 $^{35}Cl$ |
| V-9 | H | Me | H | H | S | F | H | Cl | H | 335 at 1 $^{35}Cl$ |
| V-10 | H | Me | H | H | S | Cl | H | H | Cl | 333 at 2 $^{35}Cl$ |
| V-11 | H | $CF_3$ | H | H | S | H | H | Me | H | 333 |
| V-12 | Cyclopropyl | Me | H | H | S | Cl | H | $CF_3$ | H | 407 at 1 $^{35}Cl$ |
| V-13 | Cyclopropyl | $CF_3$ | H | H | S | Cl | H | $CF_3$ | H | 461 at 1 $^{35}Cl$ |
| V-14 | H | $CF_3$ | H | H | S | F | H | F | F | 373 |
| V-15 | H | Me | H | H | S | F | H | F | F | 319 |
| V-16 | H | $CF_3$ | H | H | S | F | Me | F | F | 387 |
| V-17 | H | Me | H | H | S | F | Me | F | F | 333 |

EXAMPLES OF PROCESS FOR PREPARATION OF THE COMPOUND OF GENERAL FORMULA (I)

Example A

Preparation of N-[2-(3-Chloro-5-trifluoromethyl-pyridin-2-yl) ethyl]-2-trifluoromethyl-nicotinamide

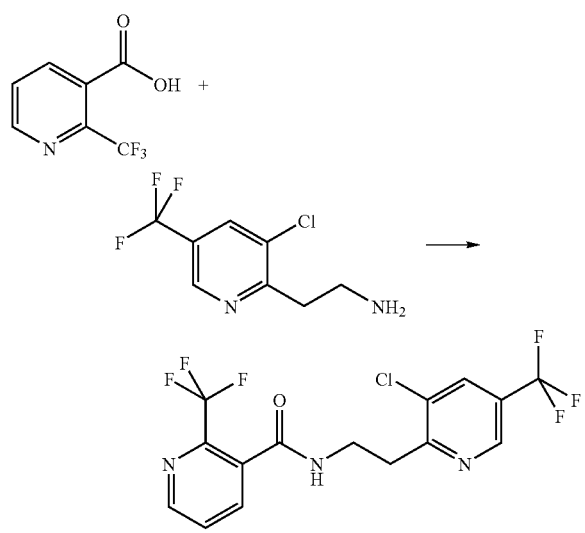

A solution of 204 mg (1 mmol) of 2-trifluormethyl nicotinic acid, 200 mg (0.9 mmol) of 2-(3-chloro-5-trifluormethyl-pyridin-2-yl)-ethylamine and 620 mg (1.3 mmol) of bromotripyrrolidinophosphonium hexafluorophosphate and 230 mg (1.8 mmol) N,N-Diisopropylethylamine in 8 ml methylene chloride is stirred for 20 h at room temperature.

The mixture is diluted with 10 ml water, separated and the methylene chloride phase is washed with sat. NH4Cl solution and water. The organic phase is dried over sodium sulfate. After evaporation of the solvent the residue is purified by column chromatography over silica-gel (eluant:hexane/ethylacetate=10:1 to 1:1). Yield: 370 mg (98%).

Example B

Preparation of 2-Chloro-N-[2-(3-chloro-5-trifluoromethyl-pyrdin-2-yl)-ethyl]-6-methyl-nicotinamide

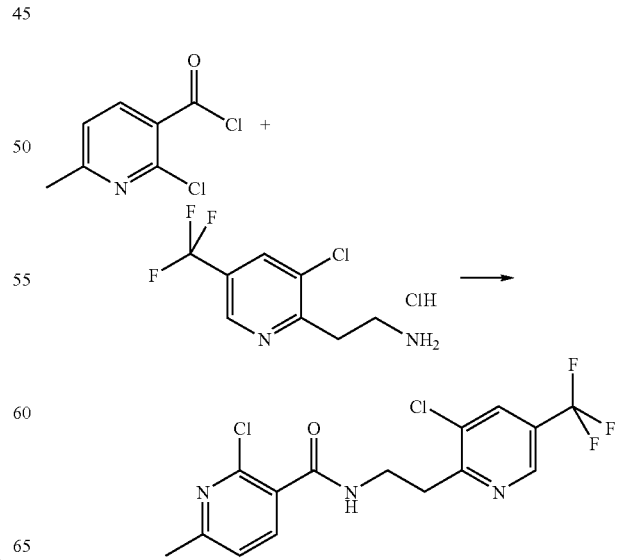

A solution of 161 mg (0.7 mmol) 2-chloro-6-methylnicotinyl chloride, 160 mg (0.7 mmol) 2-(3-chloro-5-trifluormethyl-pyridin-2-yl)-ethylamine hydrochloride and 236 mg (1.7 mmol) sodium carbonate in 8 ml acetonitrile is stirred for 3 days at room temperature.

The mixture is diluted with 5 ml water and 5 ml ethylacetate, separated and the organic phase is washed with sat. $NH_4Cl$ solution and water. The organic phase is dried over sodium sulfate and evaporated. Yield: 200 mg (62%).

Example C

Preparation of 1-Methyl-3-trifluoromethyl-1H-pyrazole4-carboxylic acid [2-(3-chloro-5-trifluoromethyl-pyridin-2-yl)-ethyl]-amide

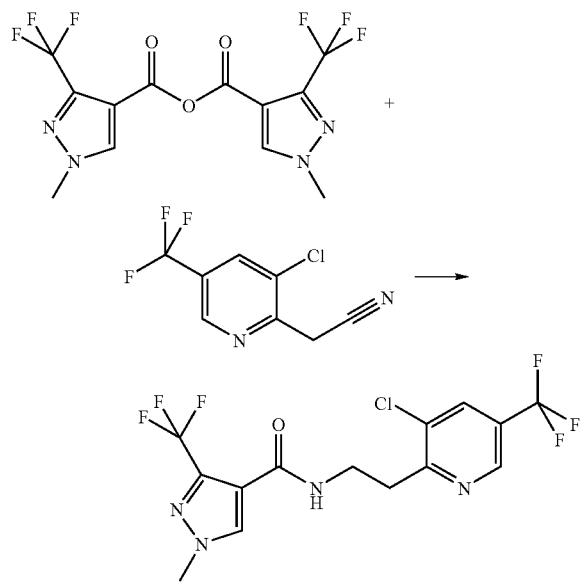

132 mg (3.5 mmol) of sodium borohydrate is added in small portions to a solution of 370 mg (1.0 mmol) 1-methyl-3-trifluoromethyl-1H-pyrazole-4-carboxylic acid-anhydride, 110 mg (0.5 mmol) (3-chloro-5-trifluormethyl-pyridin-2-yl)-acetonitrile and 120 mg (0.5 mmol) Nickel(II) chloride hexahydrate in 5 ml of acetonitrile at 0° C. Stirring was continued at room temperature for 4 hours.

After evaporation of the solvent, the residue is purified by column chromatography over silica-gel (eluant:hexane/ethylacetate=10:1 to 1:1). Yield: 80 mg (40%).

Examples of Biological Activity of the Compound of General Formula (I)

Example 1

In Vivo Test on *Alternaria brassicae* (Leaf Spot of crucifers)

The active ingredient tested is prepared by potter homogenisation in a concentrated suspension type formulation at 100 g/l. This suspension is then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per $cm^3$). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) to total protection is observed at a dose of 330 ppm with the following compounds: A-3, A-4, B-2, B-4, B-5, B-7, B-8, B-9, B-10, B-13, B-14, B-16, C-2, C-3, C-5, C-6, C-8, C-12, C-13, C-14, C-16, C-18, C-21, C-23, D-4, D-5, E-3, E-4, F-3, G-1, H-1, H-2, H-4, H-6, H-7, H-17, H-19, H-22, H-23, I-1, I-3, J-1, J-2, J-3, J-4, J-5, J-6, J-12, J-13, J-19, J-22, J-24, J-25, J-26, J-31, J-32, J-33, J-35, J-36, J-37, J-38, J-39, J-41, J-43, J-45, J-47, J-49, J-50, J-51, J-52, J-53, J-55, K-3, K-5, K-6, M -2, M-4, M-5, M-6, N-1, O-1, Q-1, Q-2, R-1, R-5, R-6, R-7, R-10, R-11, R-13, R-14, R-15, R-23, R-24, R-26, R-30, R-31, S-2, S-5, V-1, V-6, V-7, V-8, V-12.

Example 2

In Vivo Test on *Erysiphe graminis f.* sp. *tritici* (Wheat Powdery Mildew)

The active ingredient tested is prepared by potter homogenisation in a concentrated suspension type formulation at 100 g/l. This suspension is then diluted with water to obtain the desired active material concentration.

Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis f.* sp. *tritici* spores, the dusting being carried out using diseased plants. Grading is carried out 7 to 14 days after the contamination, in comparison with the control plants.

Under these conditions, good (at least 50%) to total protection is observed at a dose of 330 ppm with the following compounds: A-4, B-4, B-8, C-2, C-3, C-12, D-4, F-1, H-1, H-2, H-4, H-20, I-3, J-1, J-2, J-3, J-19, J-20, J-31, J-37, J-40, J-55, J-57, J-58, J-59, J-61, K-1, M-5, M-6, R-1, R-10, R-26, R-29, V-7.

Example 3

In Vivo Test on *Botrytis cinerea* (Cucumber Grey Mould)

The active ingredient tested is prepared by potter homogenisation in a concentrated suspension type formulation at 100 g/l. This suspension is then diluted with water to obtain the desired active material concentration.

Cucumber plants (Marketer variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatin
50 g/L of cane sugar
2 g/L of NH4NO3
1 g/L of KH2PO4

The contaminated cucumber plants are settled for 5/7 days in a climatic room at 15-11° C. (day/night) and at 80% relative humidity.

Grading is carried out 5/7 days after the contamination, in comparison with the control plants. Under these conditions, good (at least 50%) to total protection is observed at a dose of 330 ppm with the following compounds :B-7, B-8, B-13, B-14, C-3, C-12, C-13, C-14, C-15, C-16, D-4, D-5, E-4, H-1, H-2, H-4, H-7, H-9, H-22, J-1, J-2, J-3, J-19, J-31, J-32, J-33, J-34, J-35, J-37, J-39, J-43, J-44, R-1, R-10, R-23, R-24, R-26, R-31, V-1, V-8.

Example 4

In Vivo Test on *Pyrenophora teres* (Barley Net Blotch)

The active ingredient tested is prepared by potter homogenisation in a concentrated suspension type formulation at 100 g/l. This suspension is then diluted with water to obtain the desired active material concentration.

Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Pyrenophora teres* spores (12,000 spores per ml). The spores are collected from a 12-day-old culture The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 50%) to total protection is observed at a dose of 330 ppm with the following compounds A-4, B-3, B-7, B-8, B-13, B-14, B-15, B-16, C-3, C-5, C-12, C-13, C-14, C-15, C-16, C-17, C-20, C-22, C-23, D-4, D-5, E-3, E-4, F-3, G-1, H-1, H-2, H-4, H-5, H-6, H-7, H-8, H-11, H-15, H-17, H-19, H-20, H-22, H-23, I-1, I-3, J-1, J-2, J-3, J-7, J-8, J-10, J-19, J-20, J-22, J-23, J-24, J-25, J-26, J-31, J-32, J-33, J-34, J-35, J-36, J-37, J-39, J-40, J-41, J-42, J-43, J-44, J-46, J-49, J-50, J-51, J-52, J-54, J-55, J-57, J-58, J-59, J-61, K-6, M-4, P-1, R-1, R-9, R-10, R-14, R-15, R-23, R-26, R-30, R-31, S-2, V-1, V-7, V-8, V-11, V-12, V-13.

Example 5

In Vivo Test on *Peronospora brassicae* (Cabbage Downy Mildew)

The active ingredient tested is prepared by potter homogenisation in a concentrated suspension type formulation at 100 g/l. This suspension is then diluted with water to obtain the desired active material concentration.

Cabbage plants (Eminence variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Peronospora brassicae* spores (50,000 spores per ml). The spores are collected from infected plant.

The contaminated cabbage plants are incubated for 5 days at 20° C., under a humid atmosphere.

Grading is carried out 5 days after the contamination, in comparison with the control plants.

Under these conditions, good (at least 50%) to total protection is observed at a dose of 330 ppm with the following compounds :B-6, B-7, J-46, J-59.

Under these conditions, the N-{1-ethylcarbanoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-3-nitrobenzamide, the N-{1-ethylcarbamoyl-2-[3-chloro-5-(trifluoromethyl)-2-pyridinyl]ethyl}-2-bromobenzamide, the N-{1-methylcarbamoyl-2-[3-chloro-5-(trifluoromethyl)-2-pyridinyl]ethyl}methoxybenzamide and the N-{1-methylcarbamoyl-2-[3-chloro-5-(trifluoromethyl)-2-pyridinyl]ethyl}-4-phenylbenzamide disclosed by Patent Application WO 01/11965 (see respectively compounds 306, 307, 310, 315 and 316 in Table D) showed poor efficacy against *Alternaria brassicae* and *Pyrenophora teres* and no efficacy against *Botrytis cinerea* and *Peronospora parasitica* at 330 ppm.

Under these conditions, the N-{[3-chloro-5-(trifluoromethyl)-2-pyridinyl]-methyl}-5-thienylacetamide disclosed by Patent Application WO 01/11965 (see compound 101 in table B) showed poor efficacy against *Alternaria brassicae* and no efficacy against *Botrytis cinerea* and *Peronospora parasitica* at 330 ppm.

The invention claimed is:
1. A compound of the general formula (I):

in which:
X is an oxygen atom;
each Y is independently selected from the group consisting of a halogen atom, a nitro group, a cyano group, a hydroxy, C1-C6-alkoxy-C1-C6-alkylcarbonyl, a carboxyl group, a $C_1$-$C_8$-alkyl, a $C_1$-$C_6$-halogenoalkyl having 1 to 5 halogen atoms, a $C_1$-$C_8$-alkylamino, a di-$C_1$-$C_8$-alkylamino, a $C_1$-$C_8$-alkoxy, a $C_1$-$C_6$-halogenoalkoxy having 1 to 5 halogen atoms, a $C_1$-$C_8$-alkylthio, a $C_1$-$C_6$-halogenoalkylthio having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkinyloxy, a $C_3$-$C_8$-halogenoalkinyloxy having 1 to 5 halogen atoms, a $C_3$-$C_8$-cycloalkyl, a $C_1$-$C_8$-alkoxycarbonyl, a $C_1$-$C_8$-alkylsulphinyl, a $C_1$-$C_8$-alkylsulphonyl, a $C_1$-$C_8$-halogenoalkylsulphinyl having 1 to 5 halogen atoms, a $C_1$-$C_8$-halogenoalkylsulphonyl having 1 to 5 halogen atoms and a $C_1$-$C_6$-alkoximino-$C_1$-$C_6$-alkyl, provided that at least one Y substituent is a $C_1$-$C_6$-halogenoalkyl having 1 to 5 halogen atoms;

$R^1$ is selected from the group consisting of a hydrogen atom, a cyano group, a nitro group, a formyl group, a $C_1$-$C_6$-alkyl, a $C_1$-$C_6$-alkylcarbamoyl, a $C_2$-$C_6$-alkenyl, a $C_2$-$C_6$-alkynyl, a $C_1$-$C_6$-halogenoalkyl having 1 to 7 halogen atoms, a $C_1$-$C_6$-alkoxy-$C_1$-$C_6$-alkyl, a $C_1$-$C_6$-cyanalkyl, a $C_1$-$C_6$-aminoalkyl, a $C_3$-$C_6$-cycloalkyl, a $C_1$-$C_6$-alkylcarbonyl, a $C_1$-$C_6$-halogenalkylcarbonyl having 1 to 5 halogen atoms, a $C_1$-$C_6$-alkoxy-$C_1$-$C_6$-alkylcarbonyl, a $C_1$-$C_6$-alkylsulfanyl and a $C_1$-$C_6$-halogenalkylsulfanyl having 1 to 5 halogen atoms;

n is 1, 2, 3 or 4; and

Het is selected from the group consisting of substituted 6-membered heterocyclic moieties selected from the group consisting of:

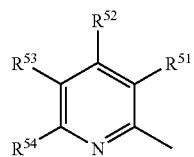

wherein:

$R^{51}$ is selected from the group consisting of a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-akylthio, a $C_1$-$C_4$-halogenoakylthio having 1 to 5 halogen atoms or a $C_1$-$C_4$-halogenoalkoxy having 1 to 5 halogen atoms;

$R^{52}$, $R^{53}$ and $R^{54}$ are independently selected from the group consisting of a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl; provided that at least one of $R^{51}$, $R^{52}$, $R^{53}$, and $R^{54}$ is not hydrogen;

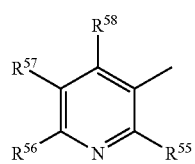

wherein:

$R^{55}$ is selected from the group consisting of a hydrogen atom, a halogen atom, a hydroxy group, a cyano group, an amino group, a $C_1$-$C_4$-alkyl, a $C_1$-$C_4$-halogenoalkyl having 1 to 5 halogen atoms, a $C_1$-$C_4$-alkoxy, a $C_1$-$C_5$-alkylthio, a $C_2$-$C_5$-alkenylthio, a $C_1$-$C_4$-halogenoalkylthio having 1 to 5 halogen atoms, a $C_1$-$C_4$-halogenoalkoxy having 1 to 5 halogen atoms, a phenyloxy optionally substituted by a halogen atom or a $C_1$-$C_4$-alkyl, or a phenylthio optionally substituted by a halogen atom or a $C_1$-$C_4$-alkyl;

$R^{56}$, $R^{57}$ and $R^{58}$ are independently selected from the group consisting of a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl, a $C_1$-$C_4$-alkylsulphonyl or a N-morpholine optionally substituted by a halogen atom or a $C_1$-$C_4$-alkyl, or a thienyl optionally substituted by a halogen atom or a $C_1$-$C_4$-alkyl; provided that at least one of $R^{55}$, $R^{56}$, $R^{57}$, and $R^{58}$ is not hydrogen; and

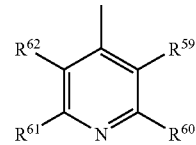

wherein $R^{59}$, $R^{60}$, $R^{61}$ and $R^{62}$ are independently selected from the group consisting of a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl or a $C_1$-$C_4$-alkylsulphonyl; provided that at least one of $R^{59}$, $R^{60}$, $R^{61}$, and $R^{62}$ is not hydrogen;

Het being linked by a carbon atom, as indicated.

2. The compound of claim 1 wherein n is 1 or 2.

3. The compound of claim 2 wherein n is 2.

4. The compound of claim 1 wherein there is at least one Y substituent that is selected from the group consisting of a halogen atom, a $C_1$-$C_8$-alkyl, and a $C_1$-$C_6$-alkoxy-$C_1$-$C_6$-alkylcarbonyl.

5. The compound of claim 1 wherein at least one Y substituent is —$CF_3$.

6. The compound of claim 1 wherein the 2-pyridyl group of the (pyridin-2-yl)-ethyl moiety is substituted in the 3- and/or in the 5-position.

7. The compound of claim 5 wherein the 2-pyridyl group of the (pyridin-2-yl)-ethyl moiety is substituted in the 5-position by —$CF_3$.

8. A fungicidal composition comprising an effective amount of a compound according to claim 1, and an agriculturally acceptable support.

9. The fungicidal composition of claim 8 further comprising a surfactant.

10. The fungicidal composition of claim 8, comprising from 0.05% to 99% by weight of the compound of formula I.

11. The compound of claim 6 wherein the 2-pyridyl group of the (pyridin-2-yl)-ethyl moiety is substituted in the 5-position by —$CF_3$.

12. The fungicidal composition of claim 9, comprising from 0.05% to 99% by weight of the compound of formula I.

13. A method for combating and/or controlling phytopathogenic fungi selected from the group consisting of *Alternaria brassicae* and *Pyrenophora teres* comprising applying an effective and non-phytotoxic amount of a compound of the general formula (I):

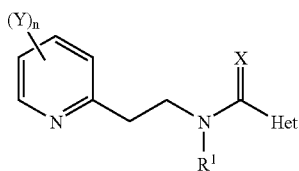

(I)

in which:
X is an oxygen atom;
each Y is independently selected from the group consisting of a halogen atom, a nitro group, a cyano group, a hydroxy, a C1-C6-alkoxy-C1-C6-alkylcarbonyl, a carboxyl group, a $C_1$-$C_8$-alkyl, a $C_1$-$C_6$-halogenoalkyl having 1 to 5 halogen atoms, a $C_1$-$C_8$-alkylamino, a di-$C_1$-$C_8$-alkylamino, a $C_1$-$C_8$-alkoxy, a $C_1$-$C_6$-halogenoalkoxy having 1 to 5 halogen atoms, a $C_1$-$C_8$-alkylthio, a $C_1$-$C_6$-halogenoalkylthio having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkinyloxy, a $C_3$-$C_8$-halogenoalkinyloxy having 1 to 5 halogen atoms, a $C_3$-$C_8$-cycloalkyl, a $C_1$-$C_8$-alkoxycarbonyl, a $C_1$-$C_8$-alkylsulphinyl, a $C_1$-$C_8$-alkylsulphonyl, a $C_1$-$C_8$-halogenoalkylsulphinyl having 1 to 5 halogen atoms, a $C_1$-$C_8$-halogenoalkylsulphonyl having 1 to 5 halogen atoms and a $C_1$-$C_6$-alkoximino-$C_1$-$C_6$-alkyl, provided that at least one Y substituent is a $C_1$-$C_6$-halogenoalkyl having 1 to 5 halogen atoms;
$R^1$ is selected from the group consisting of a hydrogen atom, a cyano group, a nitro group, a formyl group, a $C_1$-$C_6$-alkyl, a $C_1$-$C_6$-alkylcarbamoyl, a $C_2$-$C_6$-alkenyl, a $C_2$-$C_6$-alkynyl, a $C_1$-$C_6$-halogenoalkyl having 1 to 7 halogen atoms, a $C_1$-$C_6$-alkoxy-$C_1$-$C_6$-alkyl, a $C_1$-$C_6$-cyanoalkyl, a $C_1$-$C_6$-aminoalkyl, a $C_3$-$C_6$-cycloalkyl, a $C_1$-$C_6$-alkylcarbonyl, a $C_1$-$C_6$-halogenalkylcarbonyl having 1 to 5 halogen atoms, a $C_1$-$C_6$-alkoxy-$C_1$-$C_6$-alkylcarbonyl, a $C_1$-$C_6$-alkylsulfanyl and a $C_1$-$C_6$-halogenalkylsulfanyl having 1 to 5 halogen atoms;
n is 1, 2, 3 or 4; and
Het is selected from the group consisting of substituted 6-membered heterocyclic moieties selected from the group consisting of:

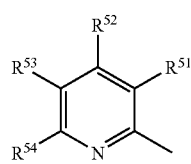

wherein:
$R^{51}$ is selected from the group consisting of a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-akylthio, a $C_1$-$C_4$-halogenoakylthio having 1 to 5 halogen atoms or a $C_1$-$C_4$-halogenoalkoxy having 1 to 5 halogen atoms;
$R^{52}$, $R^{53}$ and $R^{54}$ are independently selected from the group consisting of a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl; provided that at least one of $R^{51}$, $R^{52}$, $R^{53}$, and $R^{54}$ is not hydrogen;

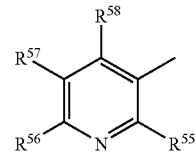

wherein:
$R^{55}$ is selected from the group consisting of a hydrogen atom, a halogen atom, a hydroxy group, a cyano group, an amino group, a $C_1$-$C_4$-alkyl, a $C_1$-$C_4$-halogenoalkyl having 1 to 5 halogen atoms, a $C_1$-$C_4$-alkoxy, a $C_1$-$C_5$-alkylthio, a $C_2$-$C_5$-alkenylthio, a $C_1$-$C_4$-halogenoalkylthio having 1 to 5 halogen atoms, a $C_1$-$C_4$-halogenoalkoxy having 1 to 5 halogen atoms, a phenyloxy optionally substituted by a halogen atom or a $C_1$-$C_4$-alkyl, or a phenylthio optionally substituted by a halogen atom or a $C_1$-$C_4$-alkyl;
$R^{56}$, $R^{57}$ and $R^{58}$ are independently selected from the group consisting of a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_1$-halogenoalkoxy having 1 to 5 halogen atoms, a $C_1$-$C_4$-alkylsulphinyl, a $C_1$-$C_4$-alkylsulphonyl or a N-morpholine optionally substituted by a halogen atom or a $C_1$-$C_4$-alkyl, or a thienyl optionally substituted by a halogen atom or a $C_1$-$C_4$-alkyl; provided that at least one of $R^{55}$, $R^{56}$, $R^{57}$, and $R^{58}$ is not hydrogen; and

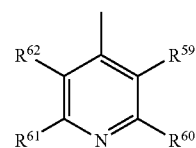

wherein
$R^{59}$, $R^{60}$, $R^{61}$ and $R^{62}$ are independently selected from the group consisting of a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl or a $C_1$-$C_4$-alkylsulphonyl; provided that at least one of $R^{59}$, $R^{60}$, $R^{61}$, and $R^{62}$ is not hydrogen;
Het being linked by a carbon atom, as indicated;
to plant seeds or to the plant leaves and/or to fruits of plants or to soil in which plants are growing or in which the plants are desired to grow.

14. The method of claim 13 wherein Het represents a heterocycle of the general formula (XXII)

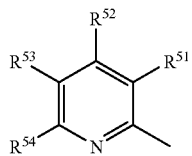

(XXII)

in which: $R^{51}$ is selected from the group consisting of a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms and a $C_1$-$C_4$-halogenoalkoxy having 1 to 5 halogen atoms; and $R^{52}$, $R^{53}$ and $R^{54}$, are independently selected from the group consisting of a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl and a $C_1$-$C_4$-alkylsulphonyl.

15. The method of claim 13 wherein Het represents a heterocycle of the general formula (XXIII)

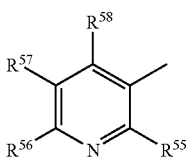

(XXIII)

in which:

$R^{55}$ is selected from the group consisting of a hydrogen atom, a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-C5-alkylthio, a $C_2$-C5-alkenylthio, a $C_1$-$C_4$-halogenoalkylthio having 1 to 5 halogen atoms, a $C_1$-$C_4$-halogenoalkoxy having 1 to 5 halogen atoms, a phenyloxy optionally substituted by a halogen atom or a $C_1$-$C_4$-alkyl, and a phenylthio optionally substituted by a halogen atom or a $C_1$-$C_4$-alkyl;

$R^{56}$, $R^{57}$ and $R^{58}$ are independently selected form the group consisting of a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkyl-sulphinyl, a $C_1$-$C_4$-alkylsulphonyl, a N-morpholine optionally substituted by a halogen atom or a $C_1$-$C_4$-alkyl, and a thienyl optionally substituted by a halogen atom or a $C_1$-$C_4$-alkyl.

16. The method of claim 13 wherein Het represents a heterocycle of the general formula (XXIV)

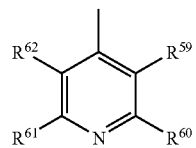

(XXIV)

in which $R^{59}$, $R^{60}$, $R^{61}$ and $R^{62}$ are independently selected from the group consisting of a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms, a $C_1$-$C_4$-halogenoalkoxy having 1 to 5 halogen atoms, a $C_1$-$C_4$-alkylsulphinyl and a $C_1$-$C_4$-alkylsulphonyl.

17. The method of claim 13 wherein n is 1 or 2.

18. The method of claim 17 wherein n is 2.

19. The method of claim 13 wherein there is at least one Y substituent that is selected from the group consisting of a halogen atom, a $C_1$-$C_8$-alkyl, and a $C_1$-$C_6$-alkoxy-$C_1$-$C_6$-alkylcarbonyl.

20. The method of claim 13 wherein at least one Y substituent is —$CF_3$.

21. The method of claim 13 wherein the 2-pyridyl group of the (pyridin-2-yl)-ethyl moiety is substituted in the 3- and/or in the 5-position.

22. The method of claim 20 wherein the 2-pyridyl group of the (pyridin-2-yl)-ethyl moiety is substituted in the 5-position by —$CF_3$.

23. The method of claim 21 wherein the 2-pyridyl group of the (pyridin-2-yl )-ethyl moiety is substituted in the 5-position by —$CF_3$.

* * * * *